United States Patent [19]

Di Bella

[11] 4,202,843

[45] May 13, 1980

[54] PROCESS FOR THE PRODUCTION OF ORGANIC PHOSPHATES BY NITRIC ACID OXIDATION OF ORGANIC PHOSPHITES

[75] Inventor: Eugene P. Di Bella, Piscataway, N.J.

[73] Assignee: Tenneco Chemicals, Inc., Saddle Brook, N.J.

[21] Appl. No.: 930,446

[22] Filed: Aug. 2, 1978

[51] Int. Cl.² ............................................. C07F 9/09
[52] U.S. Cl. ................................................. 260/985
[58] Field of Search ......................................... 260/985

[56] References Cited

U.S. PATENT DOCUMENTS 2,059,084  10/1936  Buchheim .......................... 260/985

*Primary Examiner*—Anton H. Sutto
*Attorney, Agent, or Firm*—Evelyn Berlow

[57] ABSTRACT

Organic phosphates are prepared in good yields by contacting the corresponding organic phosphites with nitric acid in the amount of at least 0.40 mole of nitric acid per mole of phosphite at a temperature in the range of 0° to 60° C.

7 Claims, No Drawings

PROCESS FOR THE PRODUCTION OF ORGANIC PHOSPHATES BY NITRIC ACID OXIDATION OF ORGANIC PHOSPHITES

This invention relates to a process for the production of organic phosphates. More particularly, it relates to a process for the production of organic phosphates by nitric acid oxidation of the corresponding phosphites.

A number of processes for the production of organic phosphates by the oxidation of organic phosphites have been reported in the literature. These processes, which employ such oxidizing agents as oxygen, ozone, hydrogen peroxide, peracids, epoxides, nitrogen oxides, and sulfur trioxide, have generally proven to be unsatisfactory for the commercial production of organic phosphates because they do not give high yields of the phosphates, because they produce substantial amounts of hydrolyzed phosphates and other undesirable reaction by-products, and because they require the use of costly reagents and processing procedures. A review of the art on the oxidation or organic phosphites to phosphates appears in "Organic Phosphorus Compounds", Volume 6, by G. M. Kosolapoff and L. Maier (New York: John Wiley and Sons, 1973), page 247 ff.

In accordance with this invention, it has been found that organic phosphates that contain only small amounts of hydrolyzed phosphates and other impurities can be prepared in high yields by contacting the corresponding organic phosphites with nitric acid. The process provides a low-cost, efficient procedure for the production of organic phosphates.

In the process of this invention, an organic phosphite is oxidized to the corresponding phosphate by contacting it with nitric acid at a temperature in the range of 0° to 60° C. The process is usually carried out by adding nitric acid to the organic phosphite while the resulting reaction mixture is being agitated sufficiently to form a uniform dispersion of the nitric acid in the phosphite. Reverse addition, that is, addition of the phosphite to the acid, gives less good results because the competitive hydrolysis reaction takes place at a faster rate in the very acidic reaction mixture.

The oxidation of the phosphites is preferably carried out at a temperature in the range of 10° to 40° C., with reaction temperatures in the range of 15° to 35° C. particularly preferred because they provide the optimum balance between the rates at which the oxidation reaction and the hydrolysis side-reaction take place.

High yields of organic phosphates that contain only small amounts of hydrolyzed materials results when the reaction mixture contains at least 0.40 mole of nitric acid per mole of phosphite. Excellent results have been obtained when from 0.45 mole to 0.55 mole of nitric acid was used per mole of phosphite. The nitric acid that is used to oxidize the phosphite may range in concentration from 1% to 114% (red fuming nitric acid), with concentrations in the range of 10% to 70% preferred. The use of 10% to 20% nitric acid is particularly preferred because it provides more rapid conversion of the phosphite to the phosphate than does more concentrated acid because the presence of a higher proportion of water in the reaction mixture favors the rate of the oxidation reaction over that of the hydrolysis reaction as well as providing better control of the reaction temperature.

The oxidation of the organic phosphites may be carried out in a solvent medium, but the use of a solvent is not necessary. The solvents that may be used are inexpensive volatile liquids that do not readily react with nitric acid under the reaction conditions, such as halogenated aliphatic hydrocarbons and aromatic hydrocarbons.

While the process is ordinarily carried out in the absence of added oxygen, oxygen or an oxygen-containing gas may be supplied to the reaction mixture during the addition of the nitric acid to increase the oxidation capacity of the latter by providing for the efficient reuse of the nitric oxide reduction products.

The organic phosphites that can be converted to the corresponding phosphates by the process of this invention are alkyl, aryl, alkaryl, and aralkyl phosphites that have very low solubility in water. These phosphites may be represented by the structural formula

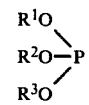

wherein $R^1$, $R^2$, and $R^3$ each represents an alkyl group having 1 to 20 carbon atoms, an aryl group having 6 to 20 cabon atoms, an aralkyl group having 7 to 20 carbon atoms, or an alkaryl group having 7 to 20 carbon atoms and the total number of carbon atoms in $R^1$, $R^2$, and $R^3$ is at least 12. Illustrative of these organic phosphites are the following: tributyl phosphite, triisohexyl phosphite, tridecyl phosphite, tridodecyl phosphite, trioctadecyl phosphite, methyl didodecyl phosphite, dibutyl decyl phosphite, diethyl dodecyl phosphite, triphenyl phosphite, tricresyl phosphite, trixylyl phosphite, phenyl dinonyl phosphite, phenyl didodecyl phosphite, decyl diphenyl phosphite, cresyl di(2-tetradecylphenyl)phosphite, tribenzyl phosphite, hexyl dibenzyl phosphite, tri(2-naphthyl)phosphite, tri(2-phenylphenyl)phosphite, and mixtures thereof. The process is of particular value in the preparation of organic phosphates by oxidation of organic phosphites having the structural formula

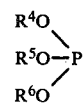

wherein $R^4$, $R^5$, and $R^6$ each represents an alkyl group having 4 to 10 carbon atoms, phenyl, or an alkylphenyl group having 7 to 10 carbon atoms. Examples of these phosphites are tributyl phosphite, tri-n-octyl phosphite, tridecyl phosphite, butyl didecyl phosphite, triphenyl phosphite, phenyl dinonyl phosphite, diphenyl decyl phosphite, tricresyl phosphite, diphenyl isopropylphenyl phosphite, phenyl di(isopropylphenyl) phosphite, and mixtures thereof. Especially good results have been obtained when the process of this invention was used in the production of triphenyl phosphate and phenyl isopropylphenyl phosphates.

When the oxidation of the organic phosphite to the corresponding organic phosphate has been completed, the acid in the reaction mixture is neutralized or removed by washing with water. The reaction mixture may then be heated under subatmospheric pressure to distill off any solvent or other volatile materials that are present. The product may be further purified, for example, by distillation or crystallization.

The fact that the conversion of organic phosphites to the corresponding phosphates can be effected with only slight competitive hydrolysis using nitric acid as the oxidizing agent is surprising in view of the well-known hydrolytic instability of organic phosphites, especially under conditions of strong acidity.

The invention is further illustrated by the following examples.

EXAMPLE 1

To a mixture of 155.1 grams (0.50 mole) of triphenyl phosphite and 80 grams of carbon tetrachloride in a flask equipped with stirrer, thermometer, and addition funnel was added dropwise, over a period of one hour, 79.3 grams (0.25 mole) of 20% nitric acid. During the addition, the reaction mixture was stirred, and sufficient external cooling to maintain a reaction temperature of 15°–20° C. was provided.

The reaction mixture separated into two phases, and the phases were separated.

The organic phase was washed with five 100 gram portions of water and then heated to 80° C./1 mm absolute pressure to remove the solvent.

There was obtained 158.2 grams of an amber oil which solidified on standing at ambient temperature. This product was shown by gas chromatographic analysis to contain 98% by weight of triphenyl phosphate and 2% by weight of phenol. On a molar basis, these data correspond to a 95.2% yield of triphenyl phosphate with only minimum (4.8%) competitive hydrolysis. The product was purified by distillation.

EXAMPLE 2

Using the procedure described in Example 1, a series of runs was carried out in which triphenyl phosphite was reacted at 15°–20° C. with nitric acid reagents of varying strength. In each run 103.4 grams (0.33 mole) of triphenyl phosphite was used, and the N/P mole ratio was only 0.3, which represents only 75% of the equivalent amount of nitric acid required, even assuming its complete reduction to molecular nitrogen as shown in the following equation:

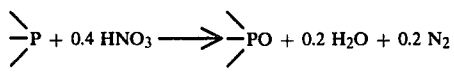

The results obtained are summarized in Table I.

Table I

| | Oxidation of Triphenyl Phosphite | | | |
|---|---|---|---|---|
| Example No. | 2A | 2B | 2C | 2D |
| Nitric Acid Concentration (%) | 20 | 35 | 70 | 114 (100% + 14% dissolved NO₂) |
| Wt. of Product (g.) | 107.4 | 107.6 | 110.4 | 108.3 |
| Composition of Product (%) | | | | |
| Phenol | 5.2 | 5.4 | 6.8 | 29.9 |
| Phosphite | 26.5 | 36.7 | 36.0 | 8.7 |
| Phosphate | 68.3 | 57.8 | 57.2 | 61.4 |
| Conversion to Phosphate (%) | | | | |
| Based on P | 67.2 | 57.3 | 58.2 | 61.2 |
| Based on N | 89.6 | 77.1 | 77.6 | 81.7 |
| Competitive Hydrolysis (%) (Based on Unrecovered phosphite & phosphate) | 3.9 | 4.5 | 3.3 | 29.7 |

The data in Table I suggest that dilute nitric acid is the preferred reagent because it effects most rapid conversion of the phosphite to the phosphate, thus minimizing the opportunity for competitive hydrolysis to occur before the oxidation has been completed.

EXAMPLE 3

A. To a mixture of 3005 grams (32 moles) of phenol, 60 grams of acid clay (Filtrol-13), and 6 grams of p-toluene-sulfonic acid was added 625 grams (14.9 moles) of propylene over a period of 8 hours during which the reaction mixture was efficiently stirred and maintained at 130°–135° C. Following a post-heating period of 3 hours at 180° C. to effect disproportionation/isomerization to a composition low in ortho substitution, the reaction mixture was cooled to 90° C. and filtered.

There was obtained 3570 grams of a phenol/isopropylphenol product (98.4% yield) having the following composition: phenol, 49.9%; o-isopropylphenyl, 20.6%; m- and p-isopropylphenols, 21.9%; 2,6-diisopropylphenol, 0.9%; other diisopropylphenols, 6.6%; and 2,4,6-triisopropylphenol, 0.1%.

To this phenol/isopropylphenol mixture was added 1375 grams (10 moles) of phosphorus trichloride over a period of 6 hours while the reaction mixture was efficiently stirred and maintained at 60°–65° C. and hydrogen chloride was evolved steadily. After the reaction mixture had been heated at 220° C. for 2 hours to complete the removal of 1116 grams of hydrogen chloride and other volatile compounds from it, it was cooled to 170° C. and vacuum was applied gradually to remove the last traces of hydrogen chloride. The reaction was then heated at 170°–175° C./1 mm to distill 289 grams of phenolic compounds from it. The residue was cooled to 90°–95° C., stirred with a mixture of 20 grams of sodium carbonate, 20 grams of clay acid (Attasorb LVM), and 20 grams of filter-aid (Celite 535) at this temperature for 1 hour, and filtered.

There was obtained in 94% yield an isopropylphenyl/phenyl phosphite composition that had an acid number of 0.01, specific gravity at 25° C. of 1.117, and viscosity at 25° C. of 37.6 centistrokes and that contained 50 ppm of labile chlorine.

B. Using the procedure described in Example 1, the isopropylphenyl/phenyl phosphite was oxidized at 30°–35° C. using either 10% or 20% nitric acid. The results obtained are summarized in Table II.

Table II

| Oxidation of Isopropylphenyl/Phenyl Phosphite | | | |
|---|---|---|---|
| Example No. | 3A | 3B | 3C |
| Batch Size (Moles Phosphite) | 0.5 | 1.25 | 0.25** |
| Nitric Acid Concentration (%) | 20 | 10 | 10 |
| Weight of Product (g.) | 169.5* | 412 | 90.6* |
| Composition of Product (%) | | | |
| Phenol | 0.4 | 10.9 | 2.3 |
| Phosphite | — | — | 4.2 |
| Phosphate | 99.6 | 89.1 | 93.5 |
| Conversion to Phosphate (%) | 88.0 | 76.6 | 88.0 |
| Competitive Hydrolysis (%) (Based on Unrecovered phosphite & phosphate) | 12.0 | 23.4 | 7.9 |

*Workup procedure included two initial washes with 200 g. portions of 1% NaOH to remove phenolic compounds.
**0.25 g. of sodium nitrite was added to the phosphite.

The data in Table II indicate that under the conditions employed the isopropylphenyl/phenyl phosphite was subjected to more hydrolysis than was the triphenyl phosphite whose oxidation is summarized in Table I, probably because of the higher reaction temperature used.

EXAMPLE 4

The procedure described in Example 1 was repeated except that the solution of triphenyl phosphite was added to the 20% nitric acid over a period of one hour while the reaction mixture was maintained at 15°–20° C.

There was obtained 154.5 grams of a product that was shown by gas chromatographic analysis to contain 82.8% by weight of triphenyl phosphate, 0.3% by weight of triphenyl phosphite, and 16.9% by weight of phenol. The yield of triphenyl phosphate was 75%. A significant amount (21.3%) of hydrolysis occurred because of the high overall acidity of the reaction mixture throughout the course of the oxidation reaction.

What is claimed is:

1. The process for the production of organic phosphates that comprises adding to an organic phosphite having the structural formula

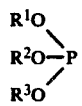

wherein $R^1$, $R^2$, and $R^3$ each represents an alkyl group having 1 to 20 carbon atoms, an aryl group having 6 to 20 carbon atoms, an aralkyl group having 7 to 20 carbon atoms, or an alkaryl group having 7 to 20 carbon atoms and the total number of carbon atoms in $R^1$, $R^2$, and $R^3$ is at least 12, 10% to 70% nitric acid in the amount of at least 0.40 mole of nitric acid per mole of phosphite at a temperature in the range of 0° to 60° C.

2. The process of claim 1 wherein 10% to 20% nitric acid is added to the phosphite.

3. The process of claim 1 wherein from 0.45 mole to 0.55 mole of the nitric acid is used per mole of the phosphite.

4. The process of claim 1 wherein the phosphite is contacted with nitric acid at a temperature in the range of 15° to 35° C.

5. The process of claim 1 wherein the organic phosphite has the structural formula

wherein $R^4$, $R^5$, and $R^6$ each represents an alkyl group having 4 to 10 carbon atoms, phenyl, or alkylphenyl having 7 to 10 carbon atoms.

6. The process of claim 1 wherein the organic phosphite is triphenyl phosphite.

7. The process of claim 1 wherein the organic phosphite is isopropylphenyl/phenyl phosphite.

* * * * *